United States Patent
Rüdenauer et al.

(10) Patent No.: US 8,853,471 B2
(45) Date of Patent: Oct. 7, 2014

(54) PROCESS FOR PREPARING C4-OXYGENATES

(71) Applicant: BASF SE, Ludwigshafen (DE)

(72) Inventors: Stefan Rüdenauer, Worms (DE); Klaus Ebel, Heddesheim (DE); Marta Porta Garcia, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/089,114

(22) Filed: Nov. 25, 2013

(65) Prior Publication Data

US 2014/0148619 A1 May 29, 2014

Related U.S. Application Data

(60) Provisional application No. 61/730,099, filed on Nov. 27, 2012.

(51) Int. Cl.
*C07C 27/00* (2006.01)
*C07C 45/00* (2006.01)
*C07C 29/44* (2006.01)

(52) U.S. Cl.
CPC ............... *C07C 29/44* (2013.01); *C07C 45/002* (2013.01)
USPC ............................ 568/904; 568/902; 568/403

(58) Field of Classification Search
USPC .......................................... 568/902, 904, 403
See application file for complete search history.

(56) References Cited

U.S. PATENT DOCUMENTS

| | | | |
|---|---|---|---|
| 1,912,695 | A | 6/1933 | Engs et al. |
| 4,380,673 | A | 4/1983 | Bournonville et al. |
| 5,723,679 | A | 3/1998 | Keshavaraja et al. |
| 8,410,293 | B2 | 4/2013 | Ebel et al. |
| 8,648,031 | B2 | 2/2014 | Ebel et al. |
| 2012/0203013 | A1 | 8/2012 | Weyrauch et al. |
| 2013/0072726 | A1 | 3/2013 | Schuch et al. |
| 2013/0137893 | A1 | 5/2013 | Ebel et al. |
| 2013/0331532 | A1 | 12/2013 | Porta Garcia et al. |
| 2014/0024854 | A1 | 1/2014 | Schaub et al. |

FOREIGN PATENT DOCUMENTS

JP 2003096004 A 4/2003

OTHER PUBLICATIONS

Zhang et al., Electron-rich PNP- and PNN-type ruthenium(II) hydrido borohydride pincer complexes. Synthesis, structure, and catalytic dehydrogenation of alcohols and hydrogenation of esters, Organometallics (2011), 30(21), 5716-5724, from CAPLUS abstract.*
Machine translation of Japanese application No. 2001-288718, filed on Sep. 2001.*
Kamitanaka, T., et al., "Direct addition of supercritical alcohols, acetone or acetonitrile to the alkenes without catalysts", Tetrahedron Letters, vol. 48, (2007), pp. 8460-8463.
Urry, W., et al., "The Peroxide- and Light-induced Additions of Alcohols to Olefins", Jacs, vol. 76, (1954), pp. 450-455.
U.S. Appl. No. 14/053,020, filed Apr. 17, 2014.
U.S. Appl. No. 14/090,626, filed Nov. 26, 2013.
U.S. Appl. No. 14/018,544, filed Mar. 13, 2014.
U.S. Appl. No. 14/022,396, filed Mar. 13, 2014.

* cited by examiner

*Primary Examiner* — Jafar Parsa
(74) *Attorney, Agent, or Firm* — Drinker Biddle & Reath LLP

(57) ABSTRACT

Preparation of $C_4$-oxygenates, in particular 2-butanol and butanone, which comprises the reaction of ethene with ethanol to form 2-butanol under conditions under which ethanol is present in the supercritical state.

8 Claims, No Drawings

PROCESS FOR PREPARING C4-OXYGENATES

CROSS-REFERENCE TO RELATED APPLICATIONS

This application claims benefit (under 35 USC 119(e)) of U.S. Provisional Application No. 61/730,099, filed Nov. 27, 2012, which is incorporated by reference.

The present invention relates to a process for preparing $C_4$-oxygenates, in particular 2-butanol and butanone, from ethane and ethanol.

Butanone, also referred to as methyl ethyl ketone or MEK, is, apart from acetone, the most important industrially produced ketone and is used as solvent in many fields. Butanone can be obtained by direct oxidation of n-butene, e.g. by the Wacker process, or as by-product from the preparation of phenol from benzene. However, the predominant proportion by far (88%) of butanone is prepared by catalytic dehydrogenation of 2-butanol. This very economical process gives high yields and displays a long life of the catalyst used, simple isolation of the product and low energy consumption. The 2-butanol used for the preparation of butanone is formed by hydration of n-butene which originates from petrochemically produced $C_4$ raffinates. (Ullmann's Encyclopedia of Industrial Chemistry, 6th edition, volume 5, pages 725-732.) A disadvantage of this process is that at least equimolar amounts of concentrated sulfuric acid are generally used (see U.S. Pat. No. 1,912,695).

The present invention provides an alternative process for the preparation of 2-butanol butanone, which starts out from ethene and ethanol. The free-radical addition of alkenes and alcohols has been known for a long time (e.g. Methoden der Organischen Chemie, Houben-Weyl, volume VI/Ib, 1984, pages 654 ff.; Urry et al., J. Am. Chem. Soc., 1954, 76: 450-455). Various processes in which free radical formation is initiated by addition of peroxides, by means of radiation or by use of the alcohol in the supercritical state (elevated pressure, elevated temperature) (Urry et al., supra; Kamitanaka et al., Tetrahedron Letters 2007, 48: 8460-8463: JP 2003-096004 A) have been described. These processes frequently lead to relatively low yields. Particularly the case of a relatively long reaction time, increasing formation of oligomers frequently takes place in such reactions and reduces the total yield. Not least for this reason, none of these processes have hitherto been used for the industrial preparation of 2-butanol and butanone.

The present invention provides a process for preparing $C_4$-oxygenates, which comprises the reaction of ethene with ethanol to form 2-butanol under conditions under which ethanol is present in the supercritical state.

2-Butanol can be obtained in high selectivity and with a good conversion by this process. The process thus represents a genuine alternative to the preparation of 2-butanol from n-butene. This was surprising because the known processes for the addition of alkenes and alcohols achieved significantly lower conversions and poorer selectivities. It was also surprising in that a gaseous starting material, viz. ethene, is used and the transition into the supercritical state therefore does not occur from a homogeneous liquid mixture but instead occurs from a liquid-gaseous two-component system.

The 2-butanol formed from ethene and ethanol can be dehydrogenated to butanone. The present invention therefore provides a process for preparing butanone from ethene and ethanol.

Ethene and ethanol are readily available, relatively inexpensive starting materials. Ethene is obtained petrochemically in large amounts. However, it can also, for example, be prepared from ethanol (Ullmann's Encyclopedia of Industrial Chemistry, 6$^{th}$ edition, volume 12, pages 532-575). This allows butanone production entirely on the basis of entirely renewable raw materials. Further advantages of the process are that no expensive and/or hazardous reagents, e.g. peroxides, radiation sources, sulfuric acid or further solvents, have to be used and the reaction proceeds highly atom-economically.

Both the conversion of ethene and ethanol into ethane and the dehydrogenation of 2-butanol to butanone, can be carried out without problems on an industrial scale and give the respective products with high selectivity and in good yields.

For the production of 2-butanol according to the invention, ethanol can be used in excess, in a substoichiometric amount or in an equimolar amount, based on ethane. It is advantageous to employ an excess of ethanol. The molar ratio of ethene used to ethanol used is preferably in the range from 1:2 to 1:1000, more preferably in the range from 1:2 to 1:500, even more preferably in the range from 1:2 to 1:200 and most preferably in the range from 1:20 to 1:150.

The process of the invention and especially the preparation according to the invention of 2-butanol can be carried out in the presence or in the substantial or complete absence of further solvents. Preference is given to not adding any further solvent. The preparation of 2-butanol according to the invention can be carried out in the presence or in the substantial or complete absence of a catalyst or initiator, e.g. a free-radical initiator such as peroxide. Preference is given to not adding any catalyst or initiator.

Substantial absence means that the concentration of further solvents, catalysts or initiators is, based on the total weight of the reaction mixture, less than 1 g/kg (<1000 ppm), in particular less than 0.1 g/kg (<100 ppm).

According to the invention, the reaction of ethene with ethanol is carried out under conditions under which ethanol is present in the supercritical state, i.e. above the critical point. The critical point of ethanol is at a temperature of 241° C. and a pressure of 6.3 MPa. In the supercritical state, liquid and gas are no longer distinguishable; the substance is present as a so-called supercritical fluid. The density of the supercritical fluid cannot be increased further by increasing the pressure. It corresponds essentially to the density in the liquid state. On the other hand, the viscosity of the supercritical fluid corresponds essentially to the viscosity in the gaseous state. The supercritical fluid thus has a relatively high density, low viscosity and high dispersibility and is an optimal solvent.

To prepare 2-butanol, ethanol or the reaction mixture composed of ethanol and ethene is heated to a temperature of 241° C. or above and subjected to a pressure of 6.3 MPa or above. For example, the ethanol can for this purpose be placed in a pressure-rated vessel, ethene can be introduced and the mixture can be heated under autogenous pressure until conditions under which ethanol is present in the supercritical state are achieved. The reaction is preferably carried out at reaction temperatures in the range 241-500° C., more preferably in the range from 250-450° C. and most preferably in the range 270-380° C., in particular in the range 280-300° C. The pressure applied is preferably in the range 6.3-50 MPa and most preferably in the range from 10 to 30 MPa, in particular in the range from 25 to 30 MPa.

The reaction time naturally depends on the conditions selected and the desired conversion. In the reaction according to the invention of ethene and ethanol, the reaction mixture is typically subjected to the reaction temperature (i.e. ≥241° C.) and the reaction pressure (i.e. ≥6.3 MPa) for a time in the range from 10 seconds to 3 hours. If desired, this procedure can be repeated once, twice, three times, four times or even more often in order to increase the conversion and thus the yield. In general, the reaction is carried out until the reactant used in a substoichiometric amount, which is preferably ethene, has been reacted to an extent of at least 80%, in particular at least 90%.

The reaction according to the invention of ethene with ethanol can be carried out batchwise (batch operation), i.e. ethanol and ethene are placed in the desired molar ratio in a suitable reactor, brought to the desired reaction conditions and maintained under the reaction conditions until the desired conversion has been reached.

The reaction according to the invention of ethene with ethanol can also be carried out in semibatch operation, i.e. the major part, in general at least 80%, in particular at least 90%, of one or both reactants is introduced into the reactor under reaction conditions either continuously or in portions over a relatively long period of time, in general at least 50% of the total reaction time. For example, at least 80%, in particular at least 90%, of the amount of ethanol used, optionally together with a partial amount of the ethene, can be placed in a reaction vessel and at least 80%, in particular at least 90%, of the ethane used can be fed to the reaction under reaction conditions.

The reaction according to the invention of ethene with ethanol can also be carried out continuously, i.e. ethene and ethanol are continuously fed in the desired molar ratio into a reaction zone and the reaction mixture is taken off continuously from the reaction zone. The rate at which ethene and ethanol are fed into the reaction zone depends on the desired residence time, which in turn depends in a known manner on the reactor geometry and corresponds to the reaction time indicated above.

The reaction according to the invention of ethene with ethanol can in principle be carried out in all reactors which are suitable for the reaction conditions selected, preferably in autoclaves, which can have devices for mixing the reactants, or in reaction tubes.

To keep the molar ratio of ethene to ethanol relatively stable during the reaction and at the same time make a particularly efficient reaction possible, it has been found to be advantageous for at least 80%, in particular at least 93%, of the ethanol used, optionally together with a partial amount of the ethene, to be placed in the reactor and at least 80%, in particular at least 90%, of the ethene used to be fed to the reaction under reaction conditions. The addition of ethene can be carried out in portions or continuously, with continuous addition being preferred. The rate at which the ethene is introduced is preferably selected so that the molar ratio of the as yet unreacted ethene fed into the reaction zone or the reactor to the ethanol present in the reaction zone is in the range from 1:2 to 1:1000, more preferably in the range from 1:2 to 1:500, particularly preferably in the range from 1:2 to 1:200 and in particular in the range from 1:20 to 1:150, during the reaction. in a continuous reaction, ethene and ethanol are therefore preferably introduced in the abovementioned molar ratios into the reactor or the reaction zone.

The reaction mixture obtained by the reaction of ethene and ethanol can be worked up in a manner known per se or, optionally after removal of the ethanol, be dehydrogenated directly as such to form butanone. The reaction mixture obtained in the reaction of ethene with ethanol can be, for example, worked up by extraction or distillation or by a combination of these measures. In an embodiment of the process of the invention, the reaction mixture obtained in the reaction of ethene with ethanol is worked up by distillation, with 2-butanol being separated off as middle fraction from low boilers and high boilers. If an excess of ethanol is employed, the low boiler fraction, which consists predominantly of ethanol, can be recirculated to the process. In general, the ethanol is largely removed before the dehydrogenation so that the proportion of ethanol in the 2-butanol-comprising product used for the dehydrogenation is less than 20% by weight, in particular not more than 10% by weight, based on the total amount of the product.

The 2-butanol obtained in the reaction of ethene with ethanol can be dehydrogenated to butanone using known processes, Such processes for oxidative dehydrogenation are described, for example, in the U.S. Pat. Nos. 5,723,679 and 4,380,673.

The dehydrogenation of 2-butanol is advantageously carried out over a suitable catalyst. Catalysts used here are usually catalysts which comprise at least one active metal selected from groups I, II, VI, VII and VIII of the Periodic Table (CAS version) and in particular from among copper, magnesium, nickel and zinc. Suitable catalysts are described, for example, in the U.S. Pat. Nos. 5,723,679 and 4,380,673. The dehydrogenation can be carried out in the gas phase, e.g. at temperatures of from 250° C. to 550° C., in particular from 300° C. to 400° C. As an alternative, the dehydrogenation can be carried out in the liquid phase, e.g. at temperatures of from 170° C. to 230° C. and using $C_{12}$-$C_{20}$-paraffinic hydrocarbons as solvent for 2-butanol. The dehydrogenation can be carried out either continuously or batchwise, with preference being given to carrying out the process continuously.

The invention is illustrated by the following examples:

EXAMPLE 1

Synthesis of 2-butanol from Ethene and Ethanol in a Batch Process 150 g of ethanol were placed in an autoclave (300 ml autoclave HC 700 bar) and a test for freedom from leaks was carried out using nitrogen, 0.91 g of ethene were subsequently infected and the reaction mixture was heated to a temperature of 290° C., with a pressure of 27 MPa being attained. After a reaction time of 2 hours under these conditions, the autoclave was cooled to room temperature and vented. The product obtained was analyzed by means of gas chromatography using 2-nonanone as internal standard. It comprised 1.4 g of 2-butanol, which based on the ethene used corresponds to a conversion of 58%. The selectivity (conversion-based yield) to 2-butanol was 90%.

EXAMPLE 2

Synthesis of 2-butanol from Ethanol and Ethylene in a Semibatch Process 150 g of ethanol were placed in an autoclave (300 ml autoclave HC 700 bar). 2 g of ethene were subsequently injected and the reaction mixture was heated to a temperature of 290° C., with a pressure of 27 MPa being attained. After a reaction time of 2 hours under these conditions, the autoclave was cooled to room temperature and vented. The injection of 2 g of ethene together with the subsequent reaction at 290° C. and 27 MPa was repeated four times. The product obtained was analyzed by means of gas chromatography using 2-nonanone as internal standard. The selectivity (conversion-based yield) to 2-butanol was 73%.

The invention claimed is:
1. A process for preparing $C_4$-oxygenates, which comprises the reaction of ethene with ethanol to form 2-butanol under conditions under which ethanol is present in the supercritical state, wherein the 2-butanol is formed at a selectivity of 73% or more.

2. The process according to claim 1, wherein ethanol is placed in a pressure-rated vessel, ethene is introduced and the mixture is heated under autogenous pressure.

3. The process according to claim 1, wherein the ethene and the ethanol are used in a molar ratio in the range from 1:2 to 1:200.

4. The process according to claim 1, wherein the reaction of ethene with ethanol takes place at a temperature in the range from 241° C. to 500° C.

5. The process according to claim 1, wherein the reaction of ethene with ethanol takes places at a pressure in the range from 6.3 MPa to 50 MPa.

6. The process according to claim 1, wherein the reaction of ethene with ethanol takes place without addition of a free-radical initiator.

7. The process according to claim 1, which further comprises dehydrogenation of the 2-butanol to form butanone.

8. The process according to claim 3, wherein the conversion to 2-butanol, based on ethene, is 58% or more.

* * * * *